(12) United States Patent
Sullinger

(10) Patent No.: US 6,708,351 B2
(45) Date of Patent: Mar. 23, 2004

(54) DRY SKIN AND CALLUS REMOVAL DEVICE

(76) Inventor: Kelly Sullinger, 2450 NE. 10th Ave., Hillsboro, OR (US) 97124

( * ) Notice: Subject to any disclaimer, the term of this patent is extended or adjusted under 35 U.S.C. 154(b) by 51 days.

(21) Appl. No.: 10/068,112

(22) Filed: Feb. 5, 2002

(65) Prior Publication Data

US 2002/0088471 A1 Jul. 11, 2002

Related U.S. Application Data

(63) Continuation-in-part of application No. 09/506,249, filed on Feb. 17, 2000, now abandoned.

(51) Int. Cl.7 .......................... A47K 3/022; A45D 29/00
(52) U.S. Cl. .................. 4/559; 4/605; 132/76.4
(58) Field of Search ........................ 4/559, 605, 606; 132/73, 76.4, 76.5

(56) References Cited

U.S. PATENT DOCUMENTS

| 5,382,189 A | * | 1/1995 | Arendall ..................... 451/557 |
| 5,658,184 A | * | 8/1997 | Hoopman et al. ............ 451/28 |
| 5,784,722 A | * | 7/1998 | Ureta et al. ..................... 4/606 |

* cited by examiner

Primary Examiner—Gregory L. Huson
Assistant Examiner—Kathleen J. Prunner
(74) Attorney, Agent, or Firm—Chernoff, Vilhauer, McClung & Stenzel, LLC

(57) ABSTRACT

A device for removing calluses and dry skin is disclosed, including a base (2) with a rim (24) and support (30) for a block of pumice (15). Base (2) also has keyholes (8) and the pumice black (15) has receiving holes (16) to accommodate suction cups (20).

5 Claims, 3 Drawing Sheets

DRY SKIN AND CALLUS REMOVAL DEVICE

This is a continuation-in-part of application Ser. No. 09/506,249, filed Feb. 17, 2000, now abandoned.

BACKGROUND OF THE INVENTION

This invention pertains to a non-hand held device for the removal of dry skin, calluses and the like from feet, elbows, hands and knees.

Prior art devices for keeping the bottoms of the human foot smooth are known. However, a common drawback of such devices is difficulty in manipulation of the device. Many prior art devices are designed to be used by hand manipulation, which is often very difficult in the case of, e.g., callus removal from a foot, for pregnant, elderly, disabled, arthritic and overweight individuals due to their inability to balance and steady themselves on one foot while manipulating the device. The device disclosed in U.S. Pat. No. 5,082,009 is designed to be held with both hands, making it extremely difficult for such classes of users to manipulate. U.S. Pat. Nos. 5,520,618 and 4,246,914 disclose devices that have no means for securing them in the shower, making their use unsafe for most who could benefit from use of such a device. U.S. Pat. Nos. 4,520,525, 5,758,381, 3,416,178, 5,228,165, 4,617,917, 5,724,695, 5,575,034, 5,437,788, 5,321,867, 5,163,200, 5,729,858, 4,003,372 and 4,047,259 all disclose foot washing and massaging devices having no capability for the removal of calluses and dry rough skin.

BRIEF SUMMARY OF THE INVENTION

The present invention comprises a base, a shaped pumice stone attached to the base, suction cups attachable to the bottom of the base and means for draining water from the device.

Important objects and advantages of the present invention include:

(a) the provision of a safe and efficient way for the hands-free removal of calluses and rough skin from, e.g., the bottom of the foot;

(b) no bending is required, allowing pregnant, elderly, overweight, arthritic or disabled persons to use it;

(c) the device is capable of placement in showers and tubs of virtually any design configuration; and (d) the device is capable of use on other body parts such as elbows, knees or hands by adjusting its placement in the shower or tub.

Other advantages of the invention include its low cost of manufacture, durability of the pumice stone as an abrasive material, no mold or bacteria build-up at the bottom of the base due to the provision of drainage holes and ease of securing the device to virtually any surface portion of a tub or shower.

DETAILED DESCRIPTION OF PREFERRED EMBODIMENT

Figure 1A:
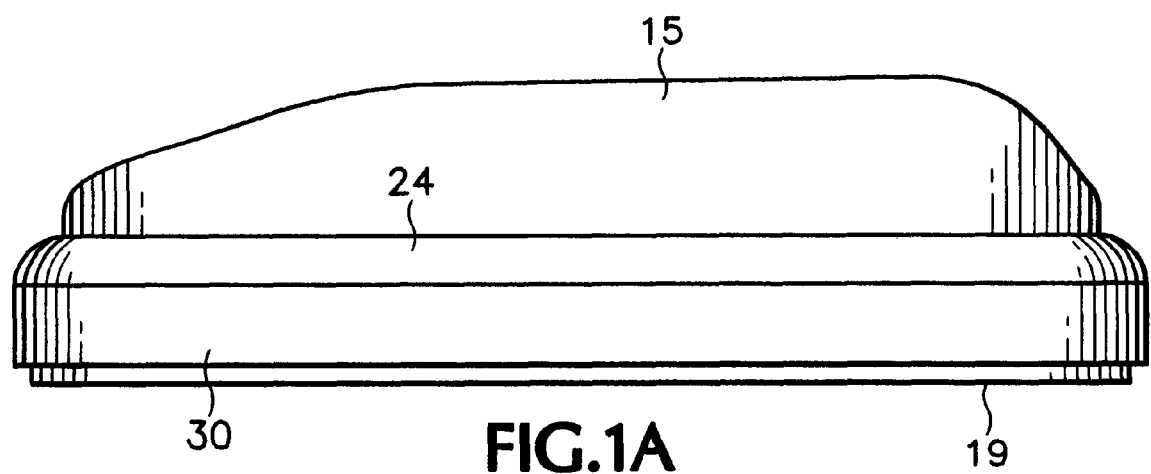
FIG. 1A is a side view.
Figure 1B:
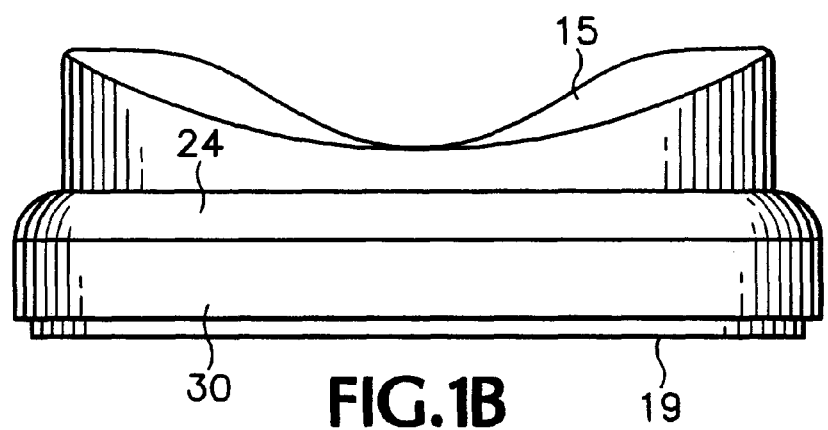
FIG. 1B is an end view showing the wide end of the pumice block.
Figure 1C:
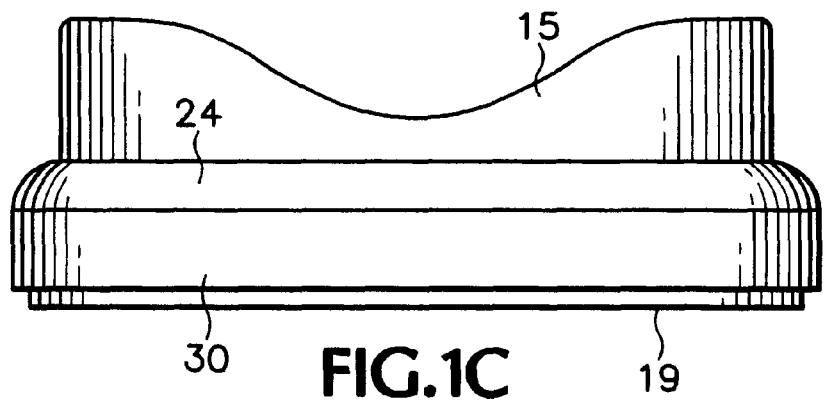
FIG. 1C is an end view showing the narrow end of the pumice block.
Figure 2A:
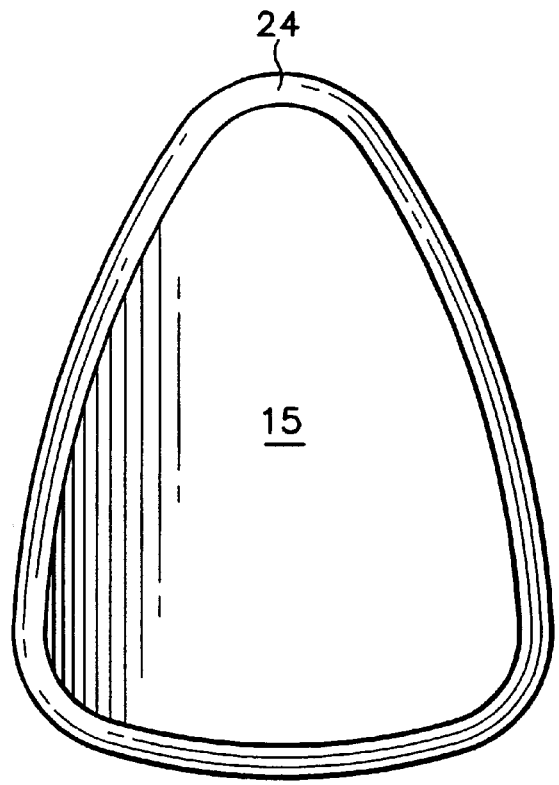
FIG. 2A is a plan view showing the pumice block surrounded by the rim on the base.
Figure 2B:
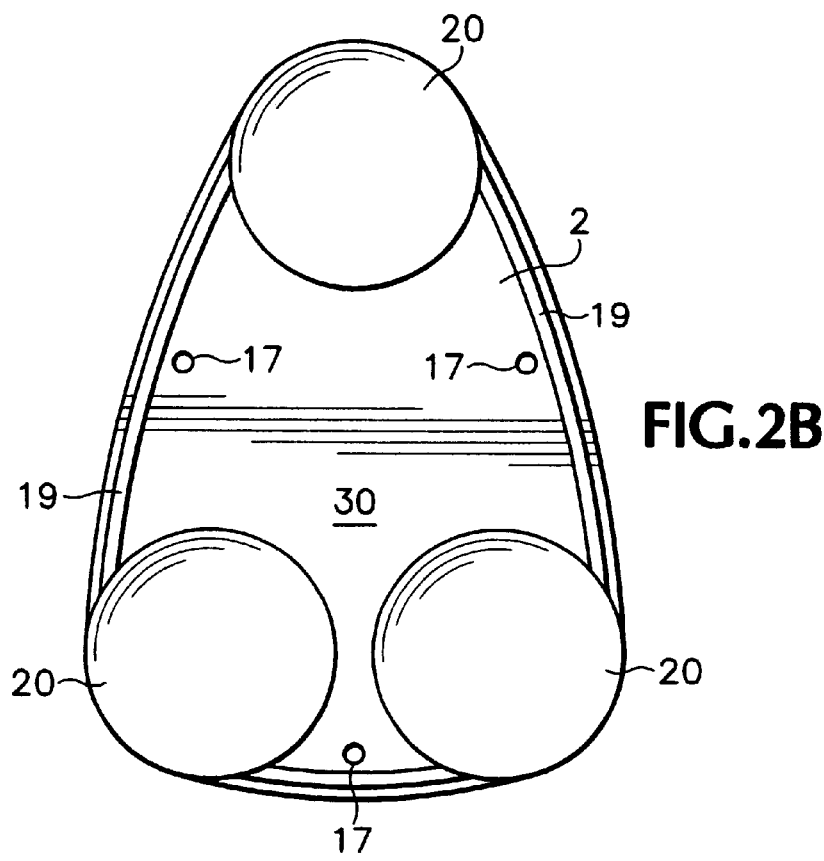
FIG. 2B is a bottom view showing the location of the suction cups, drain holes and support of the base.
Figure 3A:
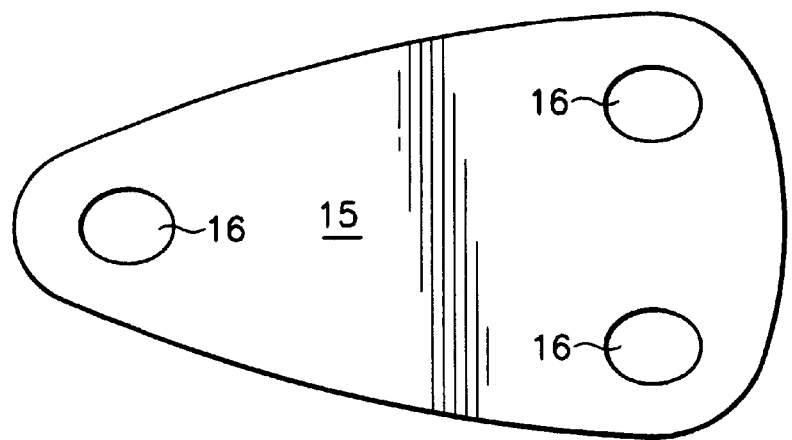
FIG. 3A is a bottom view of the pumice block.
Figure 3B:
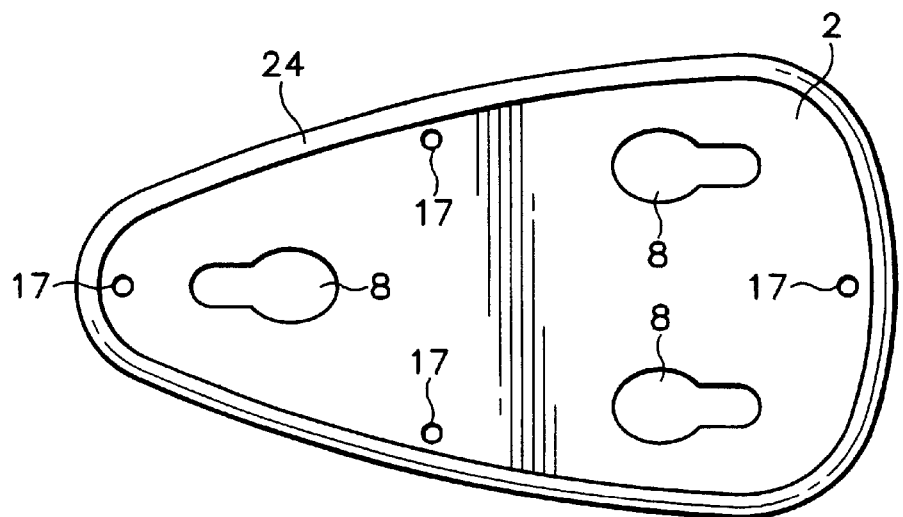
FIG. 3B is a top view of the base for the pumice block.
Figure 3C:
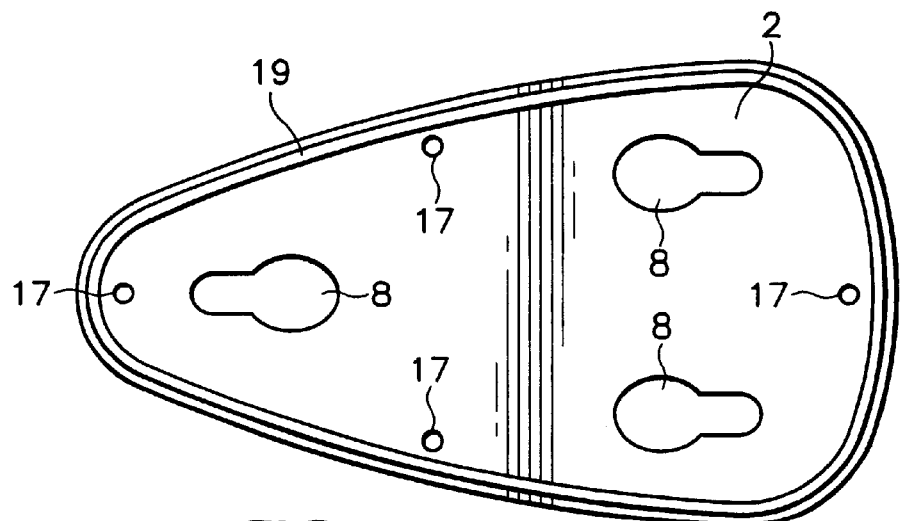
FIG. 3C is a top view of a base for the pumice block.

Referring to the drawings, wherein the same numerals refer to like elements, the device comprises a block of pumice stone 15, a planar base 2 for supporting the pumice stone and suction cups 20 to keep the device in place in a shower or tub. Pumice stone 15 has a planar lower surface for engaging base 2 and a concave upper surface to facilitate abrasion of, for example, a foot or an elbow. The pumice block is provided with receiving holes 16 on the bottom to accept the tops of suction cups 20 to ensure better support by the base. A support 30 and rim 24 around base 2 encase pumice stone 15 as well as keyholes 8 in the base 2 to insert suction cups 20 from beneath the base. Drainage holes 17 are provided in base 2 so water does not stagnate and form mold or bacteria. At the bottom of rim 24 there is a circumferential lip 19 to facilitate manual release of suction cups 20 from the surface to which they are attached. A water-insoluble glue may be used to adhere the block of pumice stone to the base.

The device can be placed on the side or bottom of a shower or tub and a body part such as a foot can be manipulated across the top of the pumice to rid that body part of dry skin and/or calluses. It can also be attached to a user's preferred position in the tub so as to permit a presoaking of the body part to be treated prior to abrading that body part with the pumice. Pumice is a preferred abrasive material, as opposed to the abrasive sheaths used in the prior art, because of its longevity, durability and superior capacity to slough off dry rough skin. A preferred material for the base is a durable resin material.

Much greater flexibility in use of the device follows from its capacity to be placed in virtually any location or at any height in a shower or a tub. Safety also is much higher due to the fact that balance will be achieved more readily by either reclining or standing while using one or both hands for support. By virtue of its semi-permanent placement in the shower or bath, one can benefit from using it more frequently, even on a daily basis, which is especially advantageous to, for example, a diabetic user, who has a need to keep extremities such as feet free of dry, rough skin and calluses and to maintain good circulation therein.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A non-hand held device for the removal of dry skin and calluses from the human body comprising:

(a) a planar base;

(b) a block formed entirely of abrasive material supported by said base, said block of abrasive material having a planar lower surface and an upper surface, the entirety of which is concave, for abrasion; and (c) a plurality of suction cups attachable to said base.

2. The device of claim 1 wherein said base is provided with keyholes through which said suction cups may be inserted.

3. The device of claim 1 wherein said base is provided with a multiplicity of drainage holes.

4. The device of claim 1 further including a lower circumferential lip on said base.

5. The device of claim 1 wherein said block of abrasive material is secured to said base by a water-insoluble glue.

* * * * *